United States Patent [19]
Ohno et al.

[11] Patent Number: 6,051,613
[45] Date of Patent: Apr. 18, 2000

[54] NITROGEN MONOXIDE PRODUCTION SUPPRESSOR

[75] Inventors: Kousaku Ohno, Tottori; Jin-emon Konishi; Seishi Suehiro, both of Hyogo, all of Japan

[73] Assignee: Nippon Zoki Pharmaceutical Co., Ltd., Osaka, Japan

[21] Appl. No.: 09/002,928

[22] Filed: Jan. 5, 1998

[30] Foreign Application Priority Data

Jan. 8, 1997 [JP] Japan ................................ 9-013146

[51] Int. Cl.⁷ ............................ A61K 35/12; A61K 35/36
[52] U.S. Cl. ...................... 514/770; 514/789; 514/921;
428/520; 428/529; 428/548; 428/553; 428/557;
428/558; 428/559; 428/563; 428/568; 428/570;
428/571; 428/572; 428/573; 428/574
[58] Field of Search .................... 514/770, 789,
514/921; 424/520, 529, 548, 553, 557,
558, 559, 563, 568, 570, 571, 572, 573,
574

[56] References Cited

U.S. PATENT DOCUMENTS

| | | | |
|---|---|---|---|
| 4,985,254 | 1/1991 | Konishi | 424/520 |
| 4,985,354 | 1/1991 | Toyomaki et al. | 435/13 |
| 5,013,558 | 5/1991 | Konishi | 424/520 |
| 5,057,324 | 10/1991 | Shibayama et al. | 424/520 |
| 5,534,509 | 7/1996 | Konishi et al. | 514/210 |
| 5,560,935 | 10/1996 | Konishi et al. | 424/520 |
| 5,767,103 | 7/1998 | Greenberg et al. | 514/52 |

FOREIGN PATENT DOCUMENTS

| | | |
|---|---|---|
| 0 300 973 | 4/1989 | European Pat. Off. |
| 0 315 591 | 10/1989 | European Pat. Off. |
| 0341 209 | 11/1989 | European Pat. Off. |
| 53-101515 | 9/1978 | Japan. |
| 57-77697 | 5/1982 | Japan. |
| 57-183720 | 11/1982 | Japan. |
| 58-35117 | 3/1983 | Japan. |
| 58-121217 | 7/1983 | Japan. |
| 62-145022 | 6/1987 | Japan. |
| 63-25600 | 5/1988 | Japan. |
| 63-39572 | 8/1988 | Japan. |
| 3-43279 | 7/1991 | Japan. |
| 3-204803 | 9/1991 | Japan. |
| 697351 | 9/1953 | United Kingdom. |

OTHER PUBLICATIONS

Takeoka, t. et al, "Influence of Neurotropin on Thymic Microenvironmental Abnormalities of NZB Mice", Int. J. Immunotherapy, XI(2), pp. 49–56 (1995).

"Drugs in Japan, Ethical Drugs", Yagkugo Jihlo Co, Ltd, 1994, p. 1434–1435.

Yokoi, et al., "Effect of Degree of Polymerization of Silicic Acid on the Gastrointestinal Absorption of Silicates in Rats", Chem. Pharm. Bull., vol. 27, No. 8, 1979, pp. 1733–1739.

*Primary Examiner*—Frederick Krass
*Attorney, Agent, or Firm*—Hollander Law Firm, P.L.C.

[57] ABSTRACT

A pharmaceutical composition containing an extract from inflammatory tissue inoculated with vaccinia virus may be used to suppress the death of cells caused by endotoxin, and suppress excessive production of nitrogen monoxide induced by endotoxin. The extract may also be used to relieve hypotension induced by endotoxin. In sepsis and other serious bacterial infectious diseases, endotoxin (an intracellular toxin) is produced and a shock symptom is induced by its action. The extract, having an excellent inhibitory action toward endotoxin-induced toxicity, is quite useful for the treatment or the prevention of endotoxin-induced shock symptoms, sepsis and various symptoms accompanied thereby. In addition, the extract has an inhibitory action towards abnormal nitrogen monoxide production during the diseased state and, therefore, it is also useful as a therapeutic and preventive agent for diseases wherein an excessive nitrogen monoxide production occurs, such as acute hypotension.

24 Claims, 3 Drawing Sheets

NITROGEN MONOXIDE PRODUCTION SUPPRESSOR

FIELD OF THE INVENTION

The present invention relates to a novel pharmacological action of an extract from inflammatory tissue inoculated with vaccinia virus. More particularly, it relates to a pharmaceutical agent such as a nitrogen monoxide production suppressor, a therapeutic agent for sepsis, an antiendotoxinic agent and a therapeutic agent for endotoxin shock containing the extract from inflammatory tissue inoculated with vaccinia virus as an effective component.

BACKGROUND OF THE INVENTION

It has been known that, against the outside invasion by virus, etc. and against the progression of inner diseases, the living body produces various biofunction-regulating substances for maintaining its bomeostasis and for regulating and normalizing the biofunctions. Two phases are involved consisting of a suppressing action to excessive reactions, and an enhancing action to depression of functions. For example, there have been various reports on biofunction-regulating substances which are produced in inflammatory tissue inoculated with vaccinia virus, methods for extracting said substances from diseased tissues, and pharmacological activities thereof, as disclosed, for example, in Japanese Examined Patent Publications Sho-63/039,572 B, published Aug. 5, 1988, Sho-63/025,600 B, published May 26, 1988, and Hei-03/043,279 B, published Jul. 1, 1991, and U.S. Pat. No. 5,013,558 to Konishi.

A commercially available drug preparation of an extract from inflammatory rabbit skin inoculated with vaccinia virus is sold in Japan under the trade name Neurotropin by Nippon Zoki Pharmaceutical Co., Osaka, Japan. As mentioned at page 1,434 of "Drugs in Japan, Ethical Drugs" (published in August of 1994; edited by Japan Pharmaceutical Information Center; published by Yakugyo Jiho Co., Ltd.), this preparation is a drug containing a non-protein active substance extracted and isolated from inflammatory tissues of rabbits inoculated with vaccinia virus. The preparation has been allowed for treatment of lower back pain, neck-shoulder-arm syndromes, periarthritis scapulohumeralis, osteoarthritis, symptomatic neuralgia, itching accompanied with skin disorders (such as eczema, dermatitis and urticaria), allergic rhinitis, sequelae of subacute myelo-optico-neuropathy (such as coldness, pain and paresthesia/dysesthesia), etc. It is approved as an ethical drug in the form of injections (subcutaneous, intramuscular and intravenous) and tablets, and is commercially available.

Neurotropin was used in an experimental study at the School of Medicine, University of California, Davis, to evaluate its influence on thymic microenvironmental abnormalities of New England black mice as reported by Y. Takeoka et al, *Int. J Immunotherapy*, XI(2), pp. 49–56 (1995). As taught by Takeoka et al, Neurotropin is a non-protein extract isolated from the inflamed dermis of rabbits inoculated with vaccinia virus and it has been reported in the literature as: 1) having beneficial effects on immune-depressed animals, 2) clinically useful as an analgesic and as an anti-allergy drug with few side-effects in humans, 3) improving the immune status of murine lupus in (NZB/NZW) F1 mice, and 4) inhibiting the development of EAE in Lewis rats, an autoimmune model of human multiple sclerosis.

As mentioned above, it is known that an extract from inflammatory tissue inoculated with vaccinia virus has various pharmacological actions such as analgesic action, sedative action, antiallergic action and action of improving peripheral circulation, as disclosed in Japanese Examined Patent Publications Sho-63/039,572 B, Sho63/025,600 B and Hei-03/043,279 B. However, there has been no report at all concerning the novel pharmacological actions of the present invention such as a suppressing action to nitrogen monoxide production, a therapeutic action for sepsis, an antiendotoxinic action, and a therapeutic action for endotoxin shock.

In sepsis and other serious bacterial infectious diseases, endotoxin (an intracellular toxin) is produced and, as a result of its action, shock symptoms occur. Endotoxin shows a variety of actions toward a living organism such as fever, leukocytosis, activation of complement and the kinin system, induction of disseminated intravascular coagulation syndrome (DIC), and suppression of bone marrow. When the shock symptoms from endotoxin progresses, an excessive hypotension, reduction of cardiac output, little urinary excretion, disturbance of consciousness, etc. are induced whereby the living body enters a very serious state. It has been suggested that a rapid hypotension upon endotoxin shock is due to excessive nitrogen monoxide which is abnormally produced by the action of endotoxin upon the vascular endothelial cells. There have been investigations on inhibitors for nitrogen monoxide synthesizing enzymes such as alginine derivatives with an object of achieving therapeutic agents for treating the hypotension resulting from the endotoxin shock.

The present inventors have conducted various tests and studies on pharmacological activity of an extract from inflammatory tissue inoculated with vaccinia virus and, as a result, they have found that said extract suppresses death of cells and excessive production of nitrogen monoxide induced by endotoxin. The extract also has an improving action toward hypotension induced by endotoxin whereupon the present invention has been achieved.

The present invention provides a pharmaceutical composition containing an extract from inflammatory tissue inoculated with vaccinia virus for use as a nitrogen monoxide production suppressor, a therapeutic agent for sepsis, an antiendotoxinic agent and a therapeutic agent for endotoxin shock.

SUMMARY OF THE INVENTION

The production of nitrogen monoxide and nitrogen monoxide synthetase caused by endotoxin is suppressed by an extract from inflammatory tissue inoculated with vaccinia virus. The extract may be used for treating or preventing a disease or condition in which abnormal levels of nitrogen monoxide are produced, such as hypotension induced by endotoxin. Serious bacterial diseases in which endotoxin is produced, such as sepsis, as well as endotoxic shock, may be treated or prevented by administering to a patient in need of such treatment or prevention a pharmaceutically effective amount of the extract from inflammatory tissue inoculated with vaccinia virus. In embodiments of the invention, the inflamed tissue may be human or animal tissue, such as tissue of a mammal, for example skin tissue of a rabbit or other mammal. Administration of the extract may, for example, be orally or by injection.

DETAILED DESCRIPTION OF THE INVENTION

Figure 1:
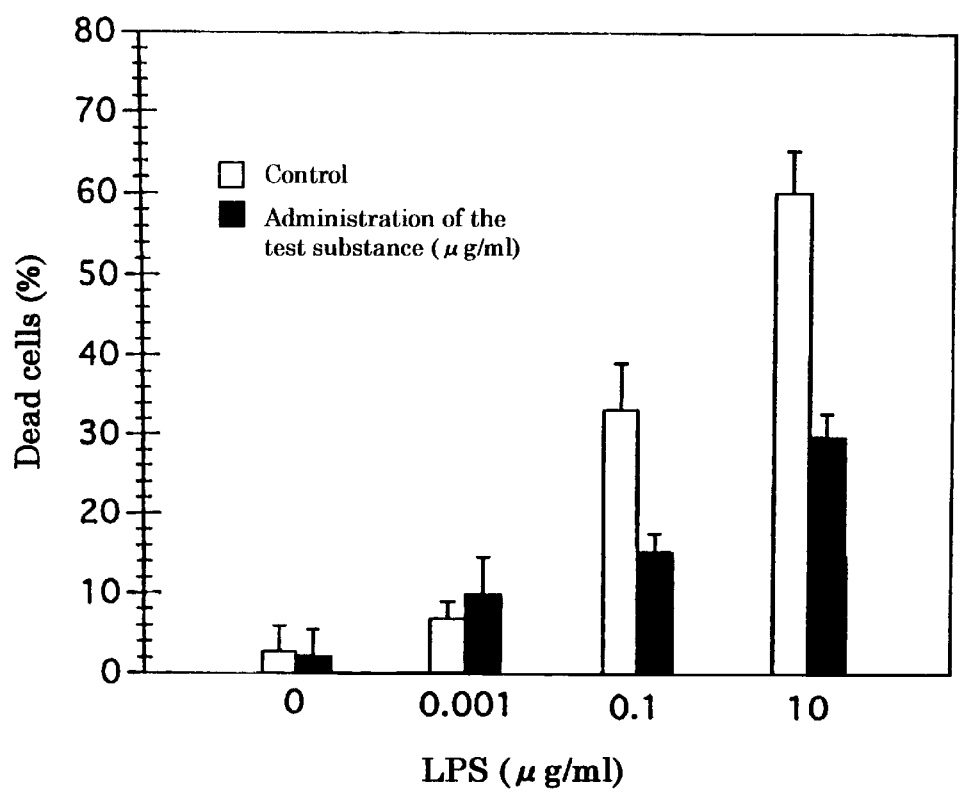
FIG. 1 shows the inhibitory effect of the substance of the present invention upon the death of endothelial cells caused by LPS.

The present invention provides a method for suppressing nitrogen monoxide production in a patient for treating or preventing a disease in which abnormal levels of nitrogen monoxide are produced. Treatment and prevention of bacterial diseases in which endotoxin is produced, such as sepsis, as well as endotoxic shock is also provided by the present invention. In accordance with the methods of the present invention, a pharmaceutical composition containing an extract from inflamed tissue as an effective component may be used as a nitrogen monoxide production suppressor, a therapeutic agent for sepsis, an antiendotoxinic agent and a therapeutic agent for endotoxin shock. Endotoxic shock symptoms such as acute hypotension caused by excessive levels of nitrogen monoxide may be treated or prevented by administration of a pharmaceutically effective amount of the extract to a patient in need thereof.

The effective component of the pharmaceutical composition of the present invention is a non-protein biofunction-regulating substance extracted from inflammatory tissues inoculated with vaccinia virus. The tissue which is inoculated may be human or animal tissue, such as tissue of a mammal, for example skin tissue of a rabbit or other mammal. Neurotropin, as discussed above, is a drug preparation of an extract from inflammatory rabbit skin inoculated with vaccinia virus which is listed in the above-mentioned "Drugs in Japan, Ethical Drugs" has been approved as a pharmaceutical agent, and is commercially available in Japan from Nippon Zoki Pharmaceutical Co., Ltd., Osaka, Japan. As discussed above, it has been the subject of several pharmaceutical studies reported in the literature, and was used in an experimental study at the School of Medicine, University of California, Davis as reported in Y. Takeoka et al, *Int. J Immunotherapy*, XI(2), pp. 49–56 (1995). The commercially available extract may be used in the compositions and methods of the present invention. The descriptions, properties and dosages of Neurotropin reported in the above-mentioned "Drugs in Japan, Ethical Drugs" and the Takeoka et al article are incorporated herein by reference in their entireties.

In addition, extracts from inflammatory tissue inoculated with vaccinia virus disclosed in Japanese Examined Patent Publications Sho-63/039,572 B, Sho-63/025,600 B and Hei-03/043,279 B and U.S. Pat. No. 5,013,558 to Konishi can be utilized as the active substance of the present invention. The extract manufacturing methods and preferred doses for use herein are also illustrated in said references. The disclosures of Japanese Examined Patent Publications Sho-63/039,572 B, Sho-63/025,600 B and Hei-03/043,279 B, and U.S. Pat. No. 5,013,558 to Konishi are herein incorporated by reference in their entireties.

A method for producing an extract from inflammatory tissue inoculated with vaccinia virus for use in the present invention is described, for example, in Example 1 of Japanese Examined Patent Publication Sho-63/039,572 B. As disclosed therein, vaccinia virus is inoculated to the skin of healthy adult rabbit. The inflamed skin is cut off under aseptic conditions and well ground. Aqueous phenol-added glycerol solution is added to this ground material and subjected to homogenization, and the emulsion is filtered by centrifugation. The resulting filtrate is adjusted to about pH 4.8–5.5, and then heated in a stream of 100° C. steam. After removing proteins thereby precipitated by filtration, the filtrate is adjusted to about pH 9.2 by addition of sodium hydroxide, heated at about 100° C. and filtered. The filtrate is adjusted to about pH 4.5 by addition of hydrochloric acid, and about 1.5% active carbon is added thereto. After stirring for about 1.5 hours, the suspension is filtered. Water is added to the resulting active carbon and the suspension is adjusted to pH 9.4–10 by addition of sodium hydroxide. The extraction procedure is carried out by stirring for about 3–5 hours. The suspension is filtered to remove the active carbon. The filtrate is adjusted to about pH 7.0–7.2 by addition of hydrochloric acid and concentrated to dryness under reduced pressure to give the extract of the present invention in a yield of about 1.5–2 g per 1 kg infected skin-tissues.

In the method of Japanese Examined Patent Publication Sho-63/025,600 B, which may be employed to produce an extract for use in the present invention, various kinds of animal tissue infected with pox obtained by inoculating a pox virus into the animals is ground, and extracted with an extracting solvent to remove a portion. The extracted solution is brought into contact with an adsorbent under acidic conditions and the adsorbed substance is eluted with water, etc. The eluate is converted into an aqueous solution, which is brought into contact with an adsorbent under acidic conditions, the adsorbed substance is eluted with a weakly basic organic solvent, etc., and the solvent is removed to give a physiologically active substance. The substance extracted from animal tissue in pox, is a light yellowish brown amorphous hygroscopic powder, soluble in water and methanol, insoluble in benzene and ether, and has a pH of 6.5–7.5, and ultraviolet absorbance of $\lambda$max=265–275 nm. It is positive in color reaction in the ninhydrin reaction, orcinol hydrochloric acid reaction, and arsenic molybdic acid method, and is negative in detection reactions for various kinds of protein.

In the method of Japanese Examined Patent Publication Hei-03/043,279 B, which may be employed to produce an extract for use in the present invention, sterilely collected tissues with poxes are ground, combined with phenol-water in an amount of 1–5 times that of the tissue to form a milk-like substance, then subjected to filtration or centrifugation. The resultant solution is adjusted in pH near its isoelectric point, heated, filtered to remove protein and made acidic with a mineral acid, then adsorbed on 5–20% activated carbon. The activated carbon is combined with an aqueous alkali to adjust its pH to 10–12, and exudation is effected under heating. The exudate is evaporated to dryness under reduced pressure or freeze dried to give the physiologically active substance.

Methods for producing extracts from inflammatory tissue inoculated with vaccinia virus for use in the present invention are also described, for example, in U.S. Pat. No. 5,013,558 to Konishi at column 1 line 44 to column 3 line 22 and in Examples 1 and 2 at column 3 lines 33 to 62, which are herein incorporated by reference in their entireties.

Thus, in accordance with the manufacturing method of U.S. Pat. No. 5,013,558 to Konishi, an extract from inflammatory tissue inoculated with vaccinia virus for use in the present invention may be prepared as follows:

(1) Inflamed or infected tissues are homogenized with an extraction medium, and tissue fragments are removed.

(2) The extracted solution thus obtained is subjected to treatment to remove proteins.

(3) An adsorbent is added to the deproteinized solution, and then the material adsorbed onto the adsorbent is eluted.

Inflamed or infected tissues may be animal tissues, organs or cultured cells inoculated or infected with vaccinia virus, a poxvirus.

To obtain the infected tissues, various kinds of animals or birds can be utilized, for example, rabbit, sheep, goat, pig, cow, horse, monkey, hamster, guinea pig, rat, mouse or hen can be employed. Also any kind of cultured cell, in which the vaccinia virus can multiply, for example, cultured cell or tumor cell of kidney, skin, lung, testis, liver, muscle, adrenal, thyroid gland, brain, nerve cell or blood cell of rabbit, sheep, goat, pig, cow, horse, monkey, hamster, guinea pig, rat, mouse, hen or their embryo, cultured cell derived from humans such as Hela cell, or decidua of the hatching egg can be employed.

The inflamed or infected tissues are collected under aseptic conditions and may be ground to as small a size as possible. An extraction medium is added to the ground material which is then homogenized. As an extraction medium, distilled water, physiological saline, weakly acidic or basic buffer, etc. may be used. A stabilizer such as glycerin, a disinfectant or preservative such as phenol, or an inorganic salt such as sodium chloride, potassium chloride or magnesium chloride can be added to the medium. At that time, the extraction can be facilitated by a procedure to disintegrate cell tissues, such as freeze-thaw extraction, sonication or treatment with a detergent or an enzyme for dissolving cell membrane.

The resulting emulsion is filtered or centrifuged to remove tissue fragments. The filtrate or supernatant is deproteinized which can be carried out according to a known method, for example, heating, sonication, treatment with a protein-denaturant such as an acid, a base, urea, guanidine, an organic solvent or a detergent, isoelectric point precipitation or salting-out technique. Subsequently, the denatured proteins thereby precipitated are removed by filtration using a filter paper such as cellulose or nitrocellulose, a glass filter, sellaite, Seitz's filter etc., ultrafiltration, gel filtration, ion-exchange chromatography or centrifugation.

The resulting extract containing the active substances is acidified, preferably to pH 3.5–5.5, by addition of an acid such as hydrochloric acid, sulfuric acid or hydrobromic acid, and then subjected to adsorption to an adsorbent such as activated carbon, kaolin or an ion-exchange resin. The adsorbent can be added to the extracted solution and stirred, or the extracted solution can be passed through a column of the adsorbent.

To elute the material containing the active substances of the present invention, a basic solution is added to the adsorbent, preferably adjusting the suspension to pH 9–12, and then the mixture is incubated or stirred at room temperature or at a suitable temperature above room temperature by heating. The elution is achieved by removing the absorbent according to a known method such as filtration or centrifugation. The eluate thus obtained, preferably after adjusting it to pH 6.5–8.5, may be concentrated to dryness under reduced pressure or lyophilized to give the extracted active substances of the present invention.

The physical and chemical properties of the physiologically active extract obtained in the above preparation are:

(1) Appearance: Pale yellowish brown and hygroscopic powder.

(2) Solubility: Soluble in water, methanol and ethanol.

(3) Ultraviolet adsorption: $\lambda max=255–275$ nm.

(4) Ninhydrine reaction: Positive.

(5) One ml of perchloric acid is added to 2 mg of the extract of the present invention, and is heated until the solution become colorless. 3 ml of dilute hydrochloric acid, 0.4 g of amidol hydrochloride and 8 g of sodium hydrogen sulfite are dissolved in 100 ml of water, and then 2 ml of the resulting aqueous solution, 1 g of ammonium molybdate and 30 ml of water are mixed. 2 ml of the mixture is added to the above solution containing the extract of the present invention. Finally, the solution shows a blue color.

(6) 5 mg of the extract of the present invention is dissolved in 10 ml of water, 0.2 g of orcine and 0.135 g of iron(II)ammonium sulfate are dissolved in 5 ml of ethanol, 83 ml of hydrochloric acid is added to the mixture, and water is added until the total becomes 100 ml. 3 ml of the resulting mixture is added to 1 ml of the above solution containing the extract of the invention and heated in a boiling water bath. Finally, the solution shows a green color.

(7) Silver nitrate reagent is added to an aqueous solution of the extract of the present invention and a precipitate is produced.

(8) Contains nucleic acid bases.

(9) Various methods of protein detection are negative.

With regard to the route of administration to the patient, subcutaneous, intramuscular and intravenous administrations by injection and oral administration by tablets are approved for the commercially available agent and may be used herein. However, it is also possible to administer pharmaceutical dosage forms other than the above-mentioned ones which are optimum for the therapy depending upon the type of the disease. The dose may depend upon the kind of extract from inflammatory tissue inoculated with vaccinia virus. The dose which is approved for the commercially available preparation according to the above "Drugs in Japan, Ethical Drugs" (page 1,434) is, principally, 16 Neurotropin units per day and 3.6–7.2 Neurotropin units per day by oral administration and by injection, respectively. The approved dose may be employed for the treatments of the present invention. However, the dose may be appropriately increased or decreased depending upon the type of the disease, degree of seriousness, individual difference in the patients, method of administration, period of administration, etc.

An extract from inflammatory tissue inoculated with vaccinia virus which is the effective component of the pharmaceutical compositions of the present invention can be made into various pharmaceutical compositions or preparations by combining one or more of the extracts with at least one pharmaceutical carrier or diluent. The extracts can be made into various types of preparations by known methods. The pharmaceutical preparations or compositions may be made into solid, semi-solid, liquid or aerosol formulations for oral administration (e.g. tablets, capsules, powders, liquids, etc.) and for parenteral administration (e.g. for subcutaneous, intravenous, intramuscular, intrarectal and intranasal administrations).

The extracts of the present invention may be used either solely or jointly in pharmaceutically effective amounts for treating animals or humans. They may also be used in pharmaceutically effective amounts in combination with pharmaceutically effective amounts of other pharmaceutically active components in pharmaceutical compositions or preparations.

In the case of parenteral administration using injections, for example, it is possible to prepare solutions or suspensions of one or more extracts of the present invention in pharmaceutically acceptable carriers such as aqueous and nonaqueous solvents such as distilled water for injection, physiological saline solution, Ringer's solution, plant oil, synthetic fatty acid glycerides, higher fatty acid esters, propylene glycol, etc.

In the case of preparations for oral administration, one or more of the extracts of the present invention alone or together with commonly-used pharmaceutically acceptable excipients in pharmaceutically acceptable amounts such as a suitable pharmaceutically acceptable additive or carrier (e.g. lactose, mannitol, corn starch, potato starch, etc.) may be mixed with one or more pharmaceutically acceptable: (1) binders such as crystalline cellulose, cellulose derivatives, gum arabicum, corn starch, gelatin, etc., (2) disintegrating agents such as corn starch, potato starch, potassium carboxymethyl-cellulose, etc., (3) lubricating agents such as talc, magnesium stearate, etc., and (4) other pharmaceutically acceptable excipients including pharmaceutically acceptable bulking agents, moisturizing agents, buffers, preservatives, perfumes and the like to obtain tablets, diluted powders, granules or capsules.

It is also possible, depending upon the type of the disease, to prepare pharmaceutical preparations other than the above-mentioned ones such as suppositories, inhalations, aerosol preparations, collyriums, ointments, poultices, etc.

For example, suppositories may be prepared by mixing at least one extract of the present invention with pharmaceutically acceptable amounts of one or more pharmaceutically acceptable fatty/oily bases (e.g. cacao butter), emulsified bases, water-soluble bases (e.g. Macrogol), hydrophilic bases, etc.

In the case of inhalations or aerosol preparations, at least one extract of the present invention in the form of a liquid or minute powder can be filled up in an aerosol container with a gas or liquid spraying agent, and if desired, with conventional adjuvants such as one or more pharmaceutically acceptable humidifying agents or dispersing agents. They can also be used as pharmaceuticals for a non-pressurized preparation such as in a nebulizer or an atomizer.

In order to make the extracts of the present invention into collyriums, they can be prepared as a solution or suspension together with an aqueous solvent such as sterile, purified water and physiologically saline solution, or a non-aqueous solvent for injection. The collyriums may also include pharmaceutically acceptable preservants, sterilizing agents, pH adjusting agents, and the like.

The present invention is further illustrated by the following non-limiting examples wherein all parts, percentages and ratios are by weight, all temperatures are in ° C., and all reactions are conducted at about atmospheric pressure unless indicated to the contrary:

EXAMPLE 1

Results of pharmacological tests demonstrating the novel pharmacological action of an extract from inflammatory tissue inoculated with vaccinia virus are:
(1) CELL PROTECTIVE ACTION Endotoxin (lipopolysaccharide: LPS) in various concentrations was added to $2 \times 10^4$ human umbilical vein endothelial cells transplanted to a 3.5 cm incubating plate and said endothelial cells were seeded. Seven days after seeding, the number of cells were counted by a hemocytometer and a measurement was conducted to determine whether the cells were alive or dead by dyeing with trypan blue. An extract from inflammatory tissue inoculated with vaccinia virus prepared by the manufacturing method described in Example 1 of Japanese Examined Patent Publication Sho-63/039,572 B, said method being herein incorporated by reference, was made to coexist with this test system.

PRODUCTION OF THE EXTRACT

In accordance with the manufacturing method described in Example 1 of Japanese Examined Patent Publication Sho-63/039,572 B, vaccinia virus is inoculated to the skin of healthy adult rabbit. The inflamed skin is cut off under aseptic conditions and well ground. Aqueous phenol-added glycerol solution is added to this ground material and subjected to homogenization, and the emulsion is filtered by centrifugation. The resulting filtrate is adjusted to about pH 4.8–5.5, and then heated in a stream of 100° C. steam. After removing proteins thereby precipitated by filtration, the filtrate is adjusted to about pH 9.2 by addition of sodium hydroxide, heated at about 100° C. and filtered. The filtrate is adjusted to about pH 4.5 by addition of hydrochloric acid, and about 1.5% active carbon is added thereto. After stirring for about 1.5 hours, the suspension is filtered. Water is added to the resulting active carbon and the suspension is adjusted to pH 9.4–10 by addition of sodium hydroxide. The extraction procedure is carried out by stirring for about 3–5 hours. The suspension is filtered to remove the active carbon. The filtrate is adjusted to about pH 7.0–7.2 by addition of hydrochloric acid and concentrated to dryness under reduced pressure to give the extract of the present invention in a yield of about 1.5–2 g per 1 kg infected skin-tissues.

EFFECT OF THE EXTRACT ON DEATH OF ENDOTHELIAL CELLS

The effect of the extract on the death of the endothelial cells by LPS was investigated. An example of the results thereof is shown in FIG. 1. As shown in FIG. 1, LPS in a concentration of more than 0.1 μg/ml damaged the endothelial cells in a dose-dependent manner resulting in death of the cells. Against such LPS-induced cell death, the extract of the present invention prepared by the above-described manufacturing method of Example 1 of Japanese Examined Patent Publication Sho-63/039,572 B showed an excellent cell protective action whereupon the survival rate of the cells was significantly improved.
(2) INHIBITORY ACTION TO NITROGEN MONOXIDE PRODUCTION As one of the action mechanisms of the cell protective action of the extract of the present invention to the above-mentioned LPS-induced cell damage, an inhibitory action to nitrogen monoxide production by LPS was investigated.

Human umbilical vein endothelial cells ($2 \times 10^4$ cells/well) were cultured on 96-well multi-plates in 200 ml of culture medium until the cells reached confluence. Then the medium was removed, a fresh medium containing LPS (0.001–100 mg/ml) and the above-described extract from inflammatory tissue inoculated with vaccinia virus prepared as described above by the manufacturing method in Example 1 of Japanese Examined Patent Publication Sho-63/039,572 B was added thereto. After 24 hours, the amount of nitrogen monoxide produced thereby was measured by means of a color development analysis using a Griess reagent. Thus, 100 ml of the incubated cells were collected from each of the incubated wells, 100 ml of a Griess reagent (a 2% phosphoric acid solution containing 1% of sulfanilamide and 0.1% of N-1-naphthylethylenediamine dihydrochloride) was added thereto, the mixture was incubated at 25° C. for ten minutes, and the absorbance (optical density: 540 nm) was measured. An aqueous solution of sodium nitrite was used as a standard solution for investigating the inhibitory action of the extract of the present invention to the nitrogen monoxide production and an example thereof is shown in FIG. 2.

Figure 2:
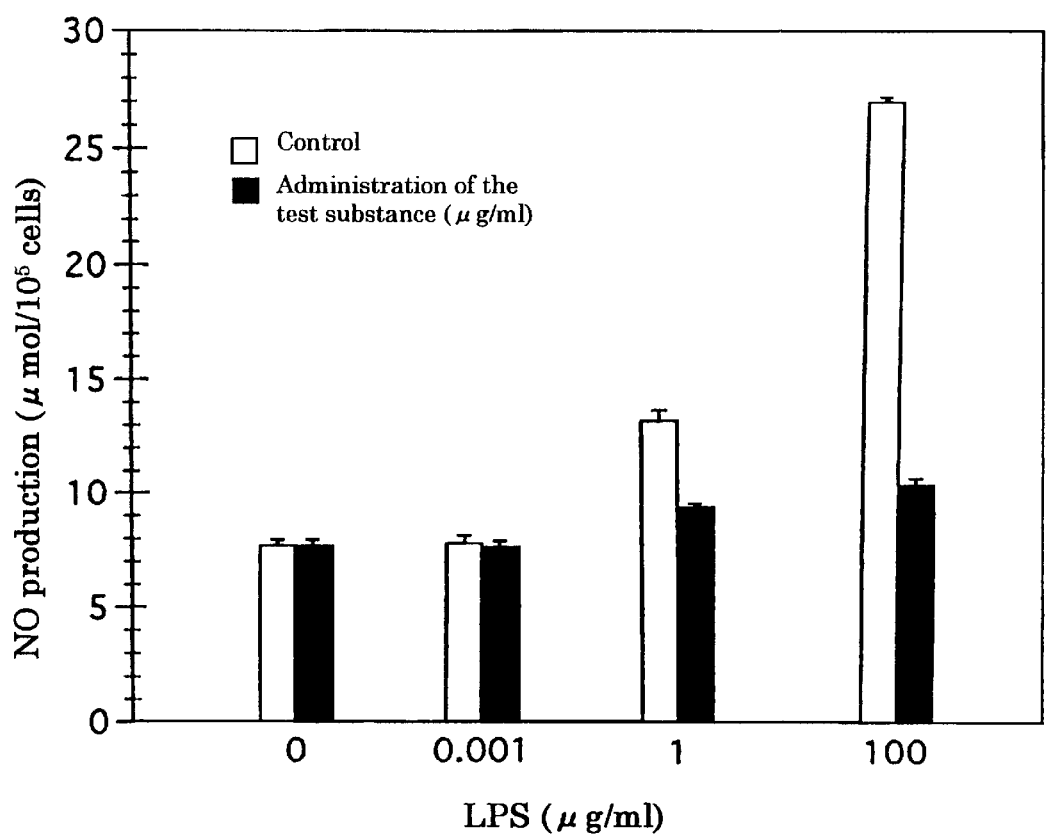
FIG. 2 shows the inhibitory action of the substance of the present invention to an excessive production of nitrogen monoxide caused by LPS.

As shown in FIG. 2, production of nitrogen monoxide significantly increased in the presence of LPS at doses higher than 0.1 μg/ml and the extract of the present invention showed substantial inhibitory action to said nitrogen monoxide production induced by LPS.

Further, the extract of the present invention (which was administered simultaneously with the administration of LPS) showed a suppressing action to an increase of NADPH-diaphorase-positive substance and an inducible nitrogen monoxide synthetase in the lung, liver and kidney of LPS-treated mice. Accordingly, it was hereby concluded that the inhibitory action of the extract of the present invention to nitrogen monoxide production was due to inhibition of an expression of the inducible nitrogen monoxide synthetase.

(3) SUPPRESSING ACTION TO LPS-INDUCED LETHAL TOXICITY

A solution of an extract of the present invention or a physiological saline solution buffered with phosphate was injected intraperitoneally to male Std;ddy mice (25–30 g) together with LPS (0.75 mg/mouse). The extract was a commercially available drug preparation sold, under the trade name Neurotropin, in Japan by Nippon Zoki Pharmaceutical Co., Osaka, Japan. The drug preparation contains non-protein active substances extracted and isolated from inflammatory rabbit skin inoculated with vaccinia virus. As discussed above, it is described at page 1,434 of "Drugs in Japan, Ethical Drugs," published in August of 1994; edited by Japan Pharmaceutical Information Center; published by Yakugyo Jiho Co., Ltd., and by Y. Takeoka et al, *Int. J Immunotherapy*, XI(2), pp. 49–56 (1995), said descriptions being incorporated herein by reference. After the initial injection, a solution of the extract of the present invention (40 units/kg) or a phosphate-buffered physiological saline solution (control) was injected every 12 hours for five days. The mortality of mice were monitored twice a day for five days. An example of the result is shown in FIG. 3.

Figure 3:
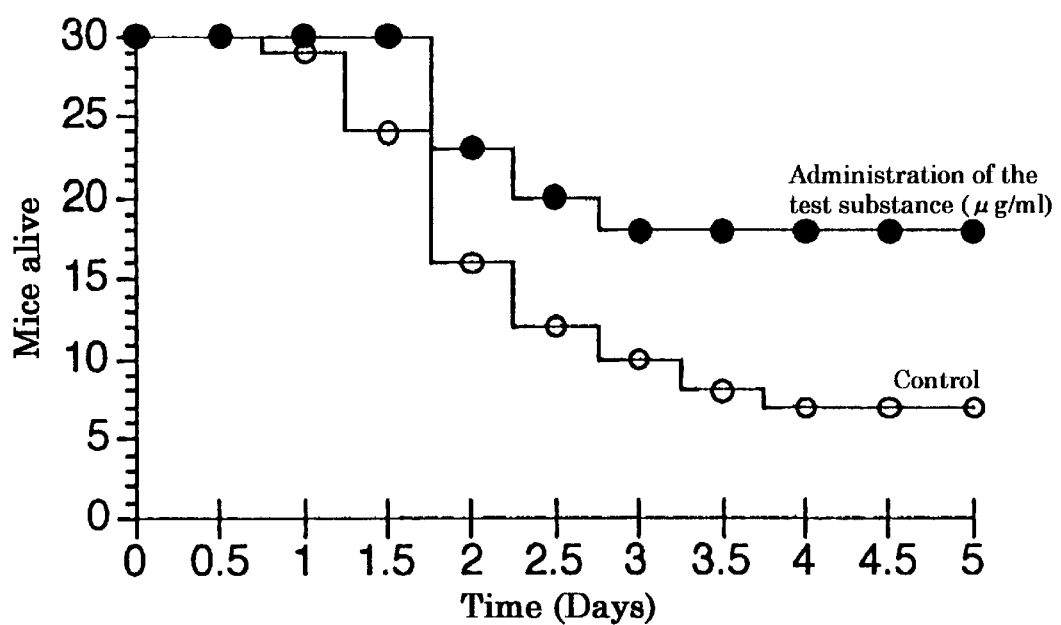
FIG. 3 shows the inhibitory action of the substance of the present invention to the lethal toxicity in mice caused by administration of LPS.

As shown in FIG. 3, survival rate of the mice injected with LPS decreased with a lapse of time. However, in the group to which the extract from inflammatory rabbit skin inoculated with vaccinia virus (the drug, Neurotropin) was administered in accordance with the present invention, a substantial suppressing action to LPS-induced lethal toxicity was observed. Thus, as in the test upon the incubated endothelial cell line shown in FIG. 1, the substantial suppressing action of the extract of the present invention to LPS-induced lethal toxicity was confirmed.

(4) IMPROVING ACTION TO LPS-INDUCED HYPOTENSION

Male Fischer rats (230–250 g) were anesthetized by an intraperitoneal injection of pentobarbital (40 mg/kg) and catheters were inserted into an artery for measurement of blood pressure and heart rate, and also for administration of the extract of the present invention. After blood pressure and heart rate stabilized, the extract of the present invention (60 mg/kg) or a physiological saline solution (control) was injected intravenously. After 30 minutes, LPS (15 mg/kg) was injected and blood pressure was measured every ten minutes for three hours. Average arterial blood pressure of the rats exposed to LPS decreased after about 40 minutes from the administration of LPS and, after 1.5–2.5 hours, a decrease of about 20% was noted. On the other hand, however, in the group to which a drug preparation of an extract from inflammatory rabbit skin inoculated with vaccinia virus was injected (Neurotropin, described above), no hypotension took place, but a slight (around 5%) hypertension was observed.

It is clear from the above-mentioned results of the pharmacological tests that an extract from inflammatory tissue inoculated with vaccinia virus which is an effective component of the pharmaceutical composition of the present invention shows an excellent preventive action to the death of cells or animals induced by endotoxin (lipopolysaccharide: LPS). The results also show a substantial inhibitory action toward excessive production of nitrogen monoxide induced by endotoxin. A sudden hypotension upon endotoxin shock is due to an excessive production of nitrogen monoxide of the vascular endothelial cells induced by endotoxin. In the above-described pharmacological test (test 4) on LPS-induced hypotension, the extract of the present invention having an inhibitory action to nitrogen monoxide production showed a preferred action of maintaining normal blood pressure against hypotension after administration of LPS.

The above-described pharmacological test results showing a suppressing action to endotoxin-induced death (test 3), an inhibitory action to nitrogen monoxide production (test 2), and an improving action to LPS-induced hypotension (test 4), are exemplary of test results obtained with various extracts from inflammatory tissues inoculated with vaccinia virus. Thus, such actions were also noted not only for the commercially available extract from inflammatory rabbit skin inoculated with vaccinia virus (Neurotropin) but also for: 1) the extracts described in the examples of Japanese Examined Patent Publication (JP) Sho-63/039,572 B, 2) the extracts described in the examples of JP Sho-63/025,600 B, and 3) the extracts described in the examples of JP Hei-03/043,279 B as well as by various other extracts from inflammatory tissue inoculated with vaccinia virus. The examples set forth in the examples of said Japanese Patent publications are herein incorporated by reference.

In sepsis and other serious bacterial infectious diseases, endotoxin (an intracellular toxin) is produced and a shock symptom is induced by its action. Accordingly, the extracts of the present invention having an excellent inhibitory action toward endotoxin-induced toxicity as mentioned above, is quite useful for the treatment or the prevention of endotoxin-induced shock symptoms, sepsis and various symptoms accompanied thereby. In addition, the extracts of the present invention have an inhibitory action toward abnormal nitrogen monoxide production during the diseased state and, therefore, are also useful as a therapeutic and preventive agent to diseases wherein an excessive nitrogen monoxide production occurs, such as acute hypotension.

We claim:

1. A method for the treatment of sepsis comprising administering to a patient in need of such treatment a pharmaceutically effective amount of an extract from inflammatory tissue inoculated with vaccinia virus.

2. A method for inhibiting endotoxin production in a patient afflicted with an endotoxin-producing disease comprising administering to said patient a pharmaceutically effective amount of an extract from inflammatory tissue inoculated with vaccinia virus.

3. A method for treating endotoxin shock comprising administering to a patient in need of such treatment a pharmaceutically effective amount of an extract from inflammatory tissue inoculated with vaccinia virus.

4. A method for the treatment of sepsis as claimed in claim 1 wherein the inflammatory tissue is a skin tissue.

5. A method for the treatment of sepsis as claimed in claim 4 wherein the inflammatory tissue is a skin tissue of a mammal.

6. A method for the treatment of sepsis as claimed in claim 1 wherein said extract is administered by injection.

7. A method for the treatment of sepsis as claimed in claim 1 wherein said extract is administered orally.

8. A method for inhibiting endotoxin production as claimed in claim 2 wherein the inflammatory tissue is a skin tissue.

9. A method for inhibiting endotoxin production as claimed in claim 8 wherein the inflammatory tissue is a skin tissue of a mammal.

10. A method for inhibiting endotoxin production as claimed in claim 2 wherein said extract is administered by injection.

11. A method for inhibiting endotoxin production as claimed in claim 2 wherein said extract is administered orally.

12. A method for treating endotoxin shock as claimed in claim 3 wherein the inflammatory tissue is an animal skin tissue.

13. A method for treating endotoxin shock as claimed in claim 12 wherein the inflammatory tissue is a skin tissue of a mammal.

14. A method for treating endotoxin shock as claimed in claim 3 wherein said extract is administered orally or by injection.

15. A method for treating hypotension caused by production of abnormal levels of nitrogen monoxide comprising administering to a patient in need of such treatment a pharmaceutically effective amount of an extract from inflammatory tissue inoculated with vaccinia virus.

16. A method as claimed in claim 15, wherein said extract is a protein free hygroscopic powder, which is soluble in methanol, ethanol and water, has an ultraviolet adsorption max of 255–275 nm, and is positive for ninhydrin reaction.

17. A method as claimed in claim 1, wherein said extract is a protein free hygroscopic powder, which is soluble in methanol, ethanol and water, has an ultraviolet adsorption max of 255–275 nm, and is positive for ninhydrin reaction.

18. A method as claimed in claim 2, wherein said extract is a protein free hygroscopic powder, which is soluble in methanol, ethanol and water, has an ultraviolet adsorption max of 255–275 nm, and is positive for ninhydrin reaction.

19. A method as claimed in claim 3, wherein said extract is a protein free hygroscopic powder, which is soluble in methanol, ethanol and water, has an ultraviolet adsorption max of 255–275 nm, and is positive for ninhydrin reaction.

20. A method as claimed in claim 15 wherein said hypotension is induced by endotoxin.

21. A method as claimed in claim 15 wherein the inflammatory tissue is a skin tissue.

22. A method as claimed in claim 21 wherein the inflammatory tissue is a skin tissue of a mammal.

23. A method as claimed in claim 15 wherein said extract is administered by injection.

24. A method as claimed in claim 15 wherein said extract is administered orally.

* * * * *